(12) United States Patent
Baid

(10) Patent No.: US 9,381,295 B2
(45) Date of Patent: Jul. 5, 2016

(54) INTRAVENOUS SET WITH AN AUTOMATIC STOPPING MECHANISM IN THE DRIP CHAMBER

(75) Inventor: Rishi Baid, New Delhi (IN)

(73) Assignee: POLY MEDICURE LIMITED, Faridabad, Haryana (IN)

( * ) Notice: Subject to any disclaimer, the term of this patent is extended or adjusted under 35 U.S.C. 154(b) by 729 days.

(21) Appl. No.: 13/266,440

(22) PCT Filed: Feb. 16, 2010

(86) PCT No.: PCT/IB2010/050698
§ 371 (c)(1),
(2), (4) Date: Oct. 26, 2011

(87) PCT Pub. No.: WO2010/125479
PCT Pub. Date: Nov. 4, 2010

(65) Prior Publication Data
US 2012/0053532 A1  Mar. 1, 2012

(30) Foreign Application Priority Data
Apr. 29, 2009 (IN) .............................. 887/DEL/2009

(51) Int. Cl.
*A61M 5/14* (2006.01)
*A61M 5/168* (2006.01)
*A61M 5/40* (2006.01)
(Continued)

(52) U.S. Cl.
CPC ............ *A61M 5/1411* (2013.01); *A61M 5/1689* (2013.01); *A61M 5/40* (2013.01); *A61M 5/162* (2013.01); *A61M 39/284* (2013.01)

(58) Field of Classification Search
CPC ............................... A61M 5/40; A61M 5/1411
USPC .................................................. 604/127, 254
See application file for complete search history.

(56) References Cited

U.S. PATENT DOCUMENTS

| | | | |
|---|---|---|---|
| 4,950,254 A | * | 8/1990 | Andersen et al. ............. 604/247 |
| 6,213,986 B1 | * | 4/2001 | Darling, Jr. ......... A61M 5/1411 137/423 |

(Continued)

FOREIGN PATENT DOCUMENTS

| | | |
|---|---|---|
| CN | 2654146 Y | 11/2004 |
| EP | 0 755 691 A1 | 1/1997 |

OTHER PUBLICATIONS

International Search Report mailed Nov. 10, 2010, from PCT Application No. PCT/IB2010/050698 (3 pages).

(Continued)

*Primary Examiner* — Emily Schmidt
(74) *Attorney, Agent, or Firm* — Kilpatrick Townsend & Stockton LLP

(57) ABSTRACT

An intravenous set with an automatic stopping mechanism in the drip chamber is provided. A top portion of the drip chamber may have a cap with a sharp tooth for puncturing a container or bottle. A lower portion of the drip chamber may be connected to a joint or stem that is connected to a flexible tube ending in a valve to be connected to a catheter. The drip chamber may contain a stopper for automatic control of fluid flow from the drip chamber. The stopper may include a lower part or diaphragm, a middle part or stem and an upper part. The stem and diaphragm may be connected by a stud, which is a part of the diaphragm. The stopper falls as the fluid flows through an exit of the drip chamber and closes the exit of the drip chamber when the fluid in the drip chamber is finished.

11 Claims, 5 Drawing Sheets

(51) Int. Cl.
*A61M 39/28* (2006.01)
*A61M 5/162* (2006.01)

(56) References Cited

U.S. PATENT DOCUMENTS 6,569,116 B1  5/2003  Wang 6,695,004 B1 *  2/2004  Raybuck ....................... 137/433

OTHER PUBLICATIONS

International Preliminary Report on Patentability mailed Nov. 10, 2011, from PCT Application No. PCT/IB2010/050698 (5 pages).
Extended European Search Report mailed Jan. 8, 2014, from European Application No. EP10769394.7 (5 pages).

\* cited by examiner

INTRAVENOUS SET WITH AN AUTOMATIC STOPPING MECHANISM IN THE DRIP CHAMBER

CROSS-REFERENCE TO RELATED APPLICATIONS

This application is a National Stage of International Application No. PCT/IB2010/050698 filed Feb. 16, 2010, and which claims the benefit of India Patent Application No. 887/DEL/2009, filed Apr. 29, 2009, the disclosures of which are incorporated herein by reference.

FIELD OF THE INVENTION

The present invention generally relates to an intravenous set. More particularly, the invention relates to an intravenous set with a flow regulating and stopping mechanism in the drip chamber.

BACKGROUND OF THE INVENTION

It would be an understatement to state the importance of the regulation and/or stopping the flow of fluids to a patient on intravenous administration. The fluids here can be of any form ranging from glucose to intravenous administration of medicines in liquid form. The flow of fluid intravenously to a patient is required to be controlled since the quantity of the fluids administered is critical for the treatment of the patient. Thus, there is a requirement that a regulating mechanism is present in an intravenous set to control the flow of fluids to the patient.

Conventional art teaches that to regulate and/or cease the flow of fluids to the patient a flow controlling device is attached to the tube connected to the patient's body. Typically, this flow control device is manual and is required to be operated by a healthcare worker to stop or regulate the flow of fluids to the patient.

This flow control device has several disadvantages such as that as soon as fluid is finished in the drip chamber, if the nurse does not close the flow regulator, air may go into the patients vein and cause air embolism and lead to severe complications including death. In normal cases, without this control device, it requires the presence of a healthcare worker at all the time near the patient to keep monitoring whether there is liquid in bottle or drip chamber and they are not empty. Another disadvantage in current case is that since the flow control device being manual depends upon the operator of the flow control device. Depending upon situation and circumstances, more or less fluid may be administered to the patient, which can have unpleasant and even fatal effect on the patient. Since there is a human element involved in the controlling of flow of fluid, there is always a possibility that the healthcare worker may forget to administer the flow control and, therefore, flow may not be stopped after the fluid is used up and consequent injecting of air into patient may take place.

SUMMARY OF THE INVENTION

It is thus an object of the present invention to provide an intravenous set with an automatic stopping mechanism in the drip chamber.

The intravenous set with an automatic stopping mechanism in the drip chamber comprises a drip chamber of wherein the top portion of the drip chamber has cap with a sharp tooth extending radially outwards for puncturing a container or bottle; wherein a lower portion of the drip chamber is connected to a joint or stem; wherein the joint or stem is connected to a flexible tube ending in a valve to be connected to a catheter; wherein the flexible tube has a manual flow control device; wherein the inside of the drip chamber contains a stopper for automatic control of flow of fluid from the drip chamber; wherein the stopper comprises of a lower part or diaphragm, a middle part or stem and a upper part; and wherein the stem and the diaphragm are connected by a flexible stud, which is a part of diaphragm.

Wherein the stopper as described is a flexible member with the outer diameter of the diaphragm is less than that of the inside diameter of the drip chamber, which may touch the inner walls of the drip chamber. The stopper has been designed in such a way that the diameter or size of the upper portion is smaller than the diameter of the diaphragm connected with a middle portion or stem by a stud. The stud allows free movement of the diaphragm while the drip chamber is slanted or shaking or abnormal dripping.

It is an object of the present invention to provide an intravenous (IV) flow controlling device disposed in a drip chamber having an exit in the bottom.

The stopper is a combination of semi-rigid and flexible material having a specific gravity less than that of the fluid in the drip chamber or in other words, the stopper floats in the fluid. The stopper is made of three parts, namely the diaphragm, the middle stem and the upper portion, wherein the diaphragm has a diameter smaller than that of the drip chamber and snugly slides along the inside walls of the drip chamber. As the fluid fills in the drip chamber the stopper is underwater and as the fluid flows through the bottom exit of the drip chamber, the stopper falls, and closes the bottom exit of the drip chamber when the fluid in the drip chamber is finished. The IV flow controlling device of the present invention functions normally even when solution is used up or there is abnormal solution dropping or the drip chamber shaken or drip chamber is slanted.

An object and advantage of the invention is that a constant fluid level in the drip chamber is always maintained even in the event of an atypical solution dropping occurs which could be due to various factors such as because of the negligence of a healthcare worker or opening of the manual flow control device or any reason which can contribute to atypical solution level dropping Another object and advantage is that the invention has been designed in such a manner that the automatic flow control device covers the space immediately left due to the atypical dropping of the level of solution in the drip chamber.

Yet another object and advantage of the invention is that the automatic stopping mechanism comes into operation and blocks the exit at the bottom of the drip chamber by creating a pressure differential and thereby attracting the automatic stopping mechanism to the region of lower pressure at the bottom of the drip chamber.

The following description of the invention accompanied by drawings shall make apparent other, in addition to the above-stated, objects, features and advantages

DETAILED DESCRIPTION OF THE PREFERRED EMBODIMENTS

Figure 1:
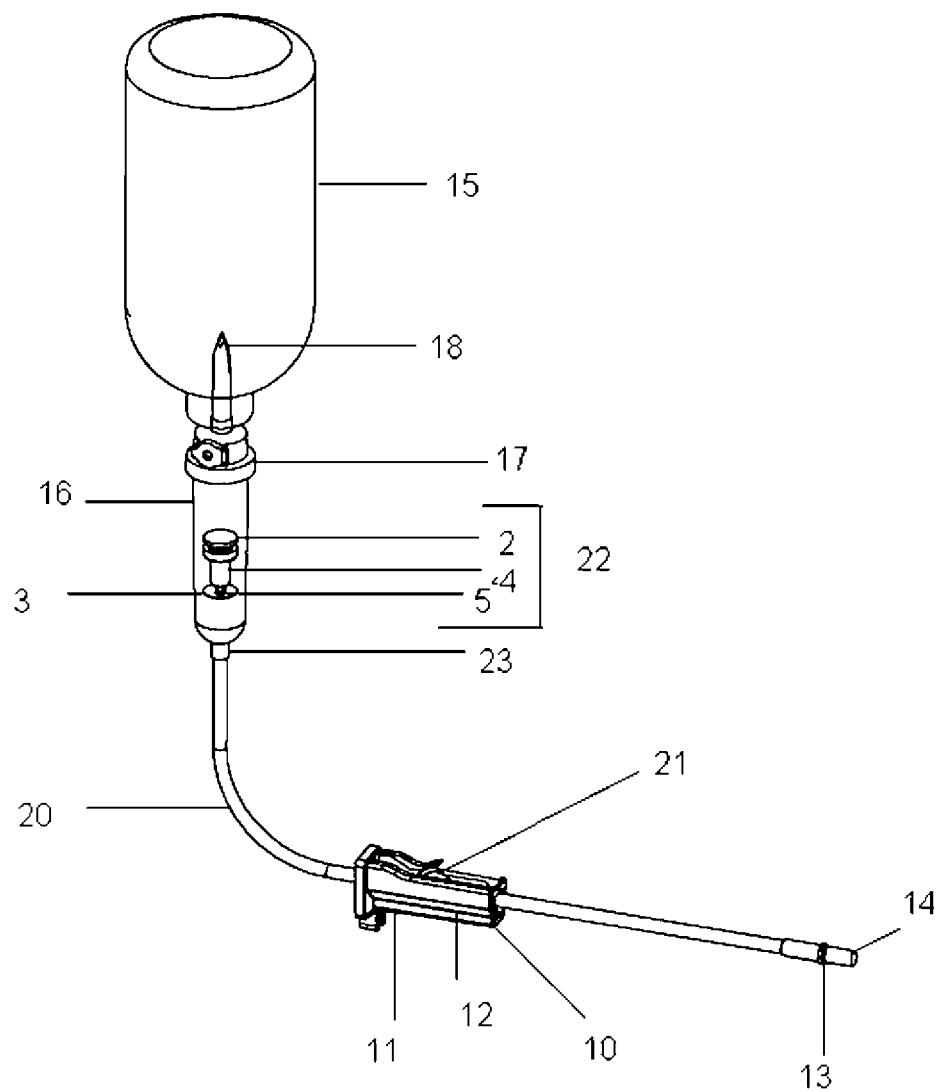
FIG. 1 is a perspective exploded view of intravenous set with an automatic stopping mechanism in the drip chamber according to the invention.

FIG. 1 depicts a preferred embodiment of an intravenous set with an automatic stopping mechanism in the drip chamber constructed in accordance with the invention. The automatic stopping mechanism is a stopper 22 disposed inside a drip chamber 16. The drip chamber 16 is connected to a cap 17 with a sharp tooth 18. The sharp tooth 18 has slits or holes for fluid to flow in to the drip chamber 16. The sharp tooth 18 is plunged or attached to a container 15 which contains the fluid to be administered. The lower portion of the drip chamber 16 has an exit 19 (not visible in this Figure but visible in all the other Figures) for the fluid to enter a tube 20. The tube 20 made of flexible material has one end connected with the drip chamber exit 19 and the other end with a valve 13 which valve 13 has a hard tube 14 as a part of its construction. This hard tube 14 attaches itself to the catheter or any other medical device that is being used to administer fluid in to a patient's body by a healthcare worker.

The tube 20 has a slidably mounted manual fluid flow control device 11 covered from the bottom with a bottom wall 10 and side wall 12. The manual flow control device 11 has the top open and is covered from three sides by walls 12 and a bottom 10. There are two openings in the manual fluid control device 11 wherein the tube 20 enters from one end and exist from the other end. The open top of the manual flow control device contains a roller 21 that slides inside the manual fluid control device 11 from one end to another. The tube 20 lies between the roller 21 and the bottom 10 of the manual flow control device and restricted in the sideway movement by the side walls 12. When the roller 21 is moved in the direction of the valve 13, the roller starts squeezing the tube 20 against the bottom 10, by which manner the flow of the fluid is controlled.

Figure 2:
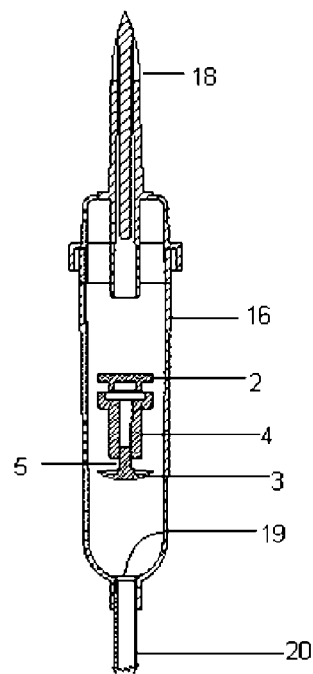
FIG. 2 is an exploded cross-sectional view of the drip chamber and the stopper within it according to the invention.
Figure 3:
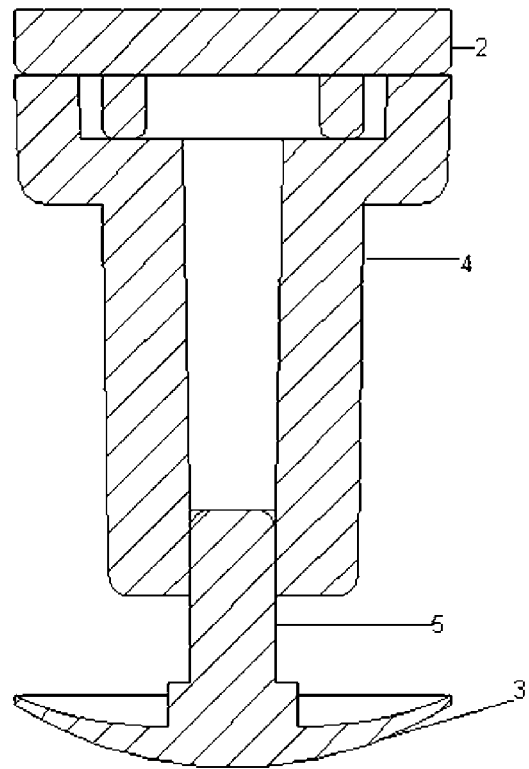
FIG. 3 is an exploded cross-sectional view of the stopper it according to the invention.
Figure 4:
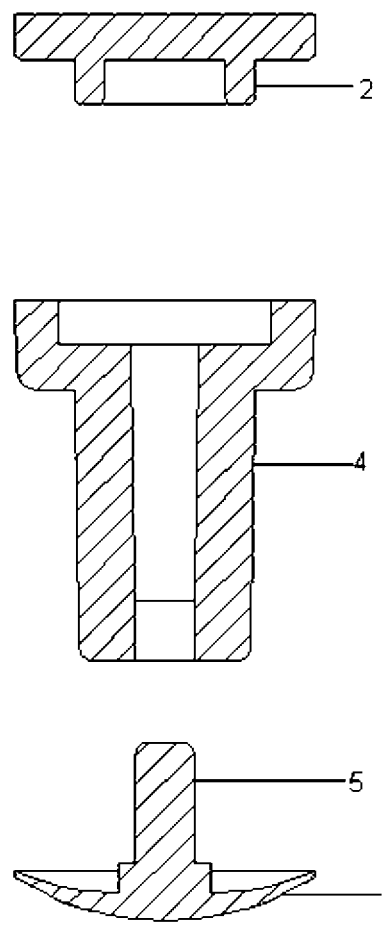
FIG. 4 is an exploded cross-sectional view of the stopper depicting the upper, middle, stud and the diaphragm according to the invention.

FIG. 2 shows the exploded cross-sectional view of the drip chamber 16 and the stopper 22 within it according to the invention. FIGS. 3 and 4 show the enlarged view of the stopper 22 and clearly represent the integral parts of the construction of the stopper 22. The stopper 22 is a semi-rigid and thin member that can be made of any flexible material such as rubber and plastic or their combination thereto. The stopper 22 comprises of four parts namely the upper part 2, the middle part or stem 4, stud 5 and the diaphragm 3. In another aspect of the invention, the stud 5 may be an integral part of the diaphragm 3. The diaphragm 3 is round and plate shaped and can be designed according to the design of the drip chamber 16. The buoyancy (capacity to float) of stopper 22 is slightly less than one (1). The upper part 2 is provided increasing the stability when the stopper 22 is submerged in fluid in the drip chamber. The outer diameter of the diaphragm 3 is slightly smaller than that of the drip chamber 16. The stud 5 is a part of the diaphragm 3 and is usually made of same flexible material such as rubber or plastic as of which the diaphragm 3 is made.

Figure 5:
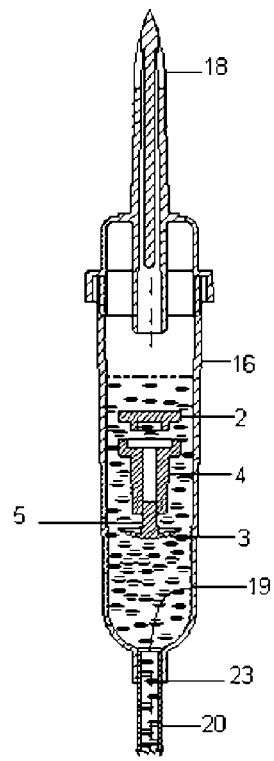
FIG. 5 is a cross-sectional view of the drip chamber filled with solution and the position of the stopper during the filling of fluid.
Figure 6:
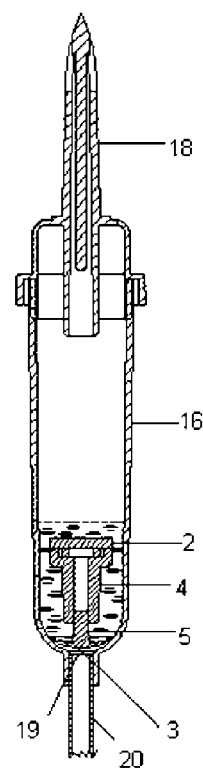
FIG. 6 is a cross-sectional view of the downward movement of the stopper as the fluid level starts dropping.

Referring to FIGS. 5 to 6, the operation of the automatic flow control device will now be described. The fluid starts flowing from the container 15 through the slits in the tooth 18 into the drip chamber 16. When the drip chamber 16 is initially empty the stopper 22 is wrapped around the exit 19. As the fluid starts filling in the drip chamber 16, the stopper 22 starts floating upwards because of buoyancy and the specific gravity of stopper being smaller than one (1). In this state, the total weight that is the weight of solution plus the weight of stopper 22 is slightly smaller than the buoyancy of fluid. The fluid flows through exit 19 in a normal dripping of solution into the tube 20 and though the manual flow controlling device 11, and then goes to a valve 14 in the end of IV the tube 20.

As the fluid exists the drip chamber 16, the fluid level starts dropping. The stopper 22, accordingly, falls due to its weight. In case of abnormal solution dropping such as excessive dripping of fluids occurs due to the carelessness of healthcare operator, the fluid level is still maintained at a constant. However, stopper 22 will immediately fall a distance due to the sensitive design of the invention. A strong suction force is formed at exit 19 when the stopper 22 falls to its lowest position, thereby causing the diaphragm 3 of the stopper 22 to block exit 19 and thereby stopping the fluid flow.

If the diaphragm 3 of the stopper 22 is not opening after blocking the exit, the simple pressing of the tube under the exit 19 disengages the stopper 22. Another manner of disengaging the stopper 22 can be by squeeze the tube 19 containing some of the fluid by hand or fingers so as to force solution stored in the tube to flow back and upward through tube 19 to disengage stopper 22 from exit 19.

FIG. 6, shows the affixing of the diaphragm 3 of the stopper 22 affixed to exit 19 by the suction of solution when solution in the drip chamber 16 is nearly used up. This stops the flow of solution.

In the preferred embodiment the stud (5) is fixed in the groove in the middle portion (4) of the stopper 22. The upper portion (2) of the stopper 22 acts as a flange for maintaining the balance of the stopper (22) in the fluid even while slanted or tilted. The balance can also be achieved by combination of the upper portion (2) and the middle portion (4) of the stopper 22 together acts as a flange for maintaining the balance of the stopper (22) in the fluid even while slanted or tilted.

Figure 7:
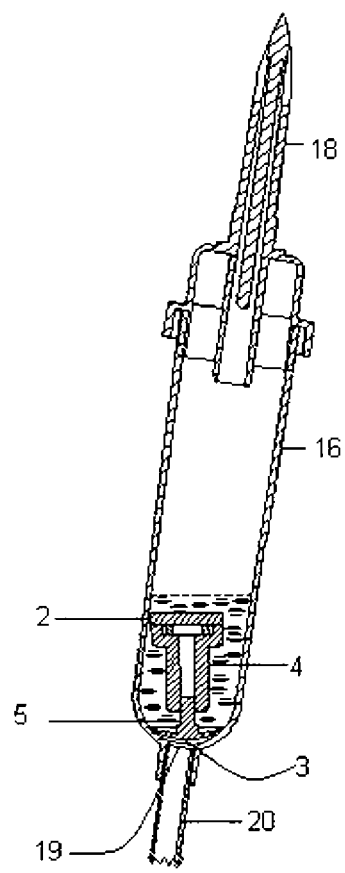
FIG. 7 depicts where the diaphragm is still completely covering the fluid exit in the drip chamber even when drip chamber and the stopper are slanted is slanted.

FIG. 7 describes and illustrates that the diaphragm 3 of stopper 22 is still fixed to fluid exit 19 even when drip chamber 16 or the stopper 22 is slanted due to shaking or any other reason. This is achieved by the stud 5 which is flexible and can move according to the position of the drip chamber 16 or the stopper 22. The functionality of the stopper 22 is still well maintained. This is one of the advantages of the invention.

Thus, there is shown and described a unique design and concept of automatic flow control device. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

The invention claimed is:

1. An intravenous set with an automatic stopping mechanism in the drip chamber comprising a drip chamber, wherein a top portion of the drip chamber has a cap with a sharp tooth extending radially outwards for puncturing a container or bottle; wherein a lower portion of the drip chamber is connected to a joint wherein the joint is connected to a flexible tube ending in a valve to be connected to a catheter; wherein the flexible tube has a manual flow control device; wherein the inside of the drip chamber contains a stopper for automatic control of flow of fluid from the drip chamber; wherein the stopper comprises a diaphragm having an outer diameter that is slightly smaller than that of the drip chamber, a stem and an upper part closing off the stem at a top; wherein the stem and the diaphragm are connected by a flexible stud which is a part of the diaphragm, the flexible stud is inserted into the stem to thereby close off the stem at a bottom of the stem; and wherein the stopper is submerged as fluid fills the drip chamber and wherein the stopper falls as the fluid flows through an exit of the drip chamber and closes the exit of the drip chamber when the fluid in the drip chamber is finished.

2. The intravenous set with an automatic stopping mechanism in the drip chamber as claimed in claim 1 wherein the stopper has a specific gravity less than one and an outer diameter smaller than the inside diameter of the drip chamber.

3. The intravenous set with an automatic stopping mechanism in the drip chamber as claimed in claim 1 wherein the stopper is made of flexible material.

4. The intravenous set with an automatic stopping mechanism in the drip chamber as claimed in claim 3 wherein the stopper is made of rubber.

5. The intravenous set with an automatic stopping mechanism in the drip chamber as claimed in claim 3 wherein the stopper is made of plastic.

6. The intravenous set with an automatic stopping mechanism in the drip chamber as claimed in claim 3 wherein the stopper is made of rubber and plastic.

7. The intravenous set with an automatic stopping mechanism in the drip chamber as claimed in claim 1 wherein the flexible stud is made of the same material as that of the diaphragm.

8. The intravenous set with an automatic stopping mechanism in the drip chamber as claimed in claim 1 wherein the flexible stud is fixed in a groove in the middle portion of the stopper.

9. The intravenous set with an automatic stopping mechanism in the drip chamber as claimed in claim 1 wherein the upper portion of the stopper acts as a flange for maintaining the balance of the stopper in the fluid even while slanted or tilted.

10. The intravenous set with an automatic stopping mechanism in the drip chamber as claimed in claim 1 wherein the upper portion and the middle portion of the stopper together act as a flange for maintaining the balance of the stopper in the fluid even while slanted or tilted.

11. The intravenous set with an automatic stopping mechanism in the drip chamber as claimed in claim 1, wherein the upper part, the hollow stem, and the flexible stud are separate component parts.

* * * * *